United States Patent [19]
Shea, Jr.

[11] 3,931,648
[45] Jan. 13, 1976

[54] STAPEDIAL PROSTHESIS
[75] Inventor: John J. Shea, Jr., Memphis, Tenn.
[73] Assignee: Richards Manufacturing Company, Memphis, Tenn.
[22] Filed: Jan. 8, 1975
[21] Appl. No.: 539,509

[52] U.S. Cl. ................................................. 3/1.9
[51] Int. Cl.² ........................ A61F 1/24; A61F 1/18
[58] Field of Search ...................... 3/1, 1.9; 128/350

[56] References Cited
UNITED STATES PATENTS

| | | | |
|---|---|---|---|
| 3,196,462 | 7/1965 | Robinson | 3/1 |
| 3,711,869 | 1/1973 | Shea, Jr. | 3/1 |
| 3,838,468 | 10/1974 | Armstrong | 3/1 |

FOREIGN PATENTS OR APPLICATIONS 117,318   3/1969   Norway........................................ 3/1

Primary Examiner—Ronald L. Frinks
Attorney, Agent, or Firm—John R. Walker, III

[57] ABSTRACT

A prosthesis for replacing a defective stapes of the middle ear. A piston is provided for transmitting sound vibrations from the incus to the oval window of the middle ear. A clamp is securely attached to the piston for anchoring the piston to the incus. The clamp is capable of being easily bent to securely grasp the incus and is capable of maintaining that bent shape after the force causing it to be bent is removed.

9 Claims, 5 Drawing Figures

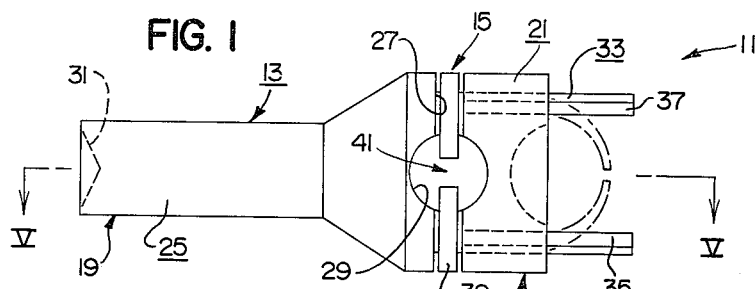
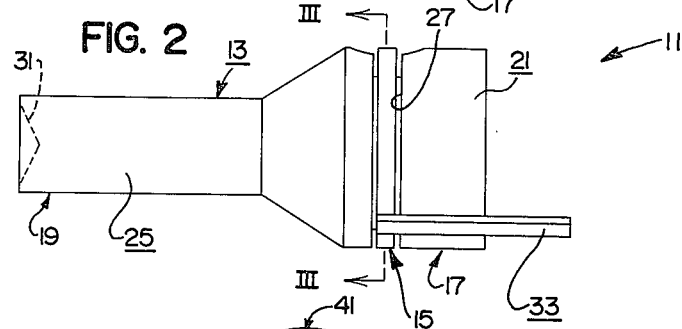
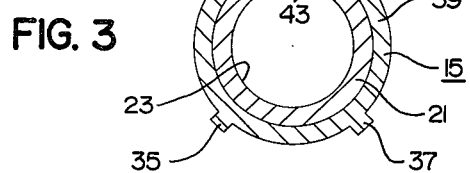
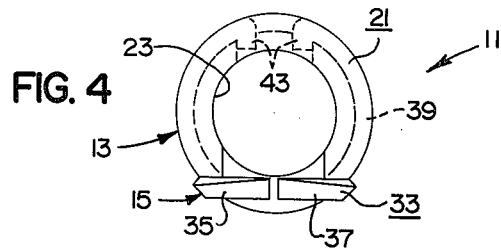
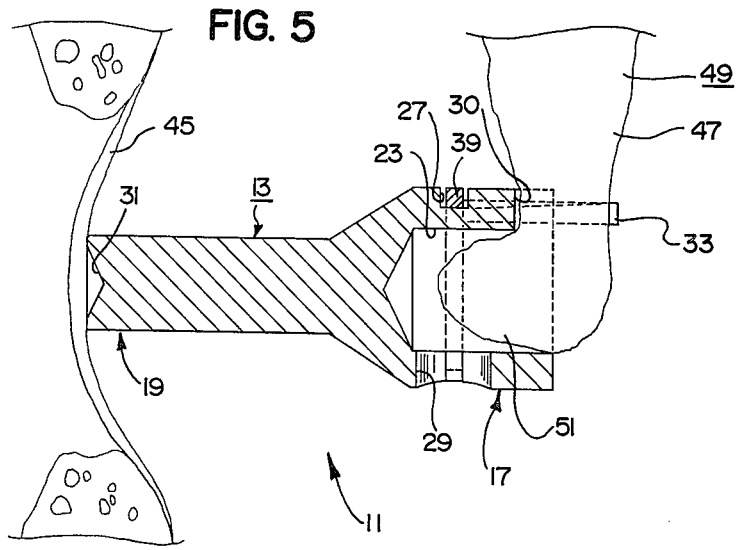

STAPEDIAL PROSTHESIS

BACKGROUND OF THE INVENTION

1. Field of the Invention

This invention relates to medical prostheses for use in otologic surgery in the middle ear.

2. Description of the Prior Art

Heretofore, various stapedial prostheses have been developed. See, for example, Mercandino et al. (U.S. Pat. No. 3,191,188), Robinson (U.S. Pat. No. 3,196,462), Shea (U.S. Pat. No. 3,711,869) and Shakhov (U.S.S.R. Pat. No. 204,496). None of the above patents disclose or suggest the present invention.

In a healthy ear, the stapes extends from the lenticular process of the incus to the oval window for transmitting sound vibrations from the incus to the oval window. Due to various reasons, the stapes sometimes becomes defective and is replaced by a stapedial prosthesis. A major problem with all prior stapedial prostheses concerns the securing of the prosthesis to the incus. The Robinson prosthesis disclosed in U.S. Pat. No. 3,196,462 utilizes a wire loop for securing the prosthesis onto the incus. In this type prosthesis, there is the possibility of pressure necrosis (deadening or killing of bone cells) if the wire loop is applied too tightly and the possibility of dislocation of the prosthesis if the wire loop is applied too loosely. The Shea prosthesis disclosed in U.S. Pat. No. 3,711,869 overcomes the problem of pressure necrosis by having a socket provided in the head of the prosthesis which closely receives a portion of the lenticular process of the incus to secure the prosthesis to the incus. In this prosthesis, a loop extends from the head portion of the prosthesis and fits around the long process of the incus to insure that the prosthesis is held to the incus in the event that the portion of the lenticular process is dislodged from the socket. The loop does not normally contact the incus. In such a prosthesis there is the possibility of dislocation, resulting at best in inefficient transmission of sound vibrations from the incus to the oval window.

SUMMARY OF THE INVENTION

The stapedial prosthesis of the present invention is directed towards overcoming the problems and disadvantages of prior stapedial prostheses. The concept of the present invention is to provide a prosthesis that can be easily, securely and safely anchored to the incus.

The prosthesis of the present invention includes piston means for transmitting sound vibrations from the incus to the oval window of the middle ear and anchor means securely attached to the piston means for anchoring the piston means to the incus. The anchor means includes a clamp member for extending substantially around the incus to fixedly attach the piston means to the incus. The clamp member is capable of being easily bent to securely grasp the incus and is capable of maintaining that bent shape after the force causing it to be bent is removed. The portion of the clamp member that extends around the incus is substantially flat and wide (as compared to the wire loop of Robinson) to prevent the possibility of pressure necrosis. The end of the piston means adjacent the oval window when the piston means is anchored to the incus may be provided with an indent for allowing the membrane covering the oval window of the middle ear to grow thereinto thereby helping the piston means to maintain its proper position relative to the oval window.

BRIEF DESCRIPTION OF THE DRAWINGS

FIG. 1 is an enlarged front elevational view of the stapedial prosthesis of the present invention.

FIG. 2 is an enlarged side elevational view of the stapedial prosthesis of the present invention.

FIG. 3 is a sectional view of the stapedial prosthesis of the present invention as taken on line III—III of FIG. 2.

FIG. 4 is an end elevational view of the stapedial prosthesis of the present invention.

FIG. 5 is a sectional view of the stapedial prosthesis of the present invention as taken on line V—V of FIG. 1 diagrammatically showing the present invention in place in the middle ear.

DESCRIPTION OF THE PREFERRED EMBODIMENT

The stapedial prosthesis 11 of the present invention is for use in otologic surgery in the middle ear to replace the stapes. The stapedial prosthesis 11 includes, in general, piston means 13 for transmitting sound vibrations from the incus to the oval window of the middle ear and includes anchor means 15 for anchoring the piston means 13 to the incus.

The piston means 13 includes a first end 17 for engagement with the incus and includes a second end 19 for association with the oval window. The first end 17 of the piston means 13 preferably includes a head portion 21 having a socket 23 for receiving a portion of the lenticular process of the incus. The second end 19 of the piston means 13 includes a preferably cylindrical rod portion 25. The socket 23 preferably has its longitudinal axis aligned with the longitudinal axis of the rod portion 25 and opens opposite the second end 19 of the piston means 13. The head portion 21 preferably includes a groove 27 in its outer wall lying transverse to the longitudinal axis of the socket 23. An aperture 29 preferably extends laterally from the socket 23 through one wall of the head portion 21 adjacent the groove 27 for allowing access into the socket 23 when a portion of the lenticular process of the incus in received in the socket 23. The rim of the head portion 21 may be provided with a channel 30 or the like for receiving a portion of the long process of the incus. The channel 30, among other things, helps center the incus relative to the longitudinal axes of the socket 23 and rod portion 25. The rod portion 25 of the second end 19 of the piston means 13 preferably includes an indent 31 opening opposite from the socket 23 of the head portion 21 for allowing the membrane covering the oval window of the middle ear to grow thereinto thereby helping the piston means 13 to maintain its proper position relative to the oval window. The piston means 13 may be constructed of any biocompatible material well known to those skilled in the art. More specifically, the piston means 13 may be constructed of stainless steel, Teflon, or the like. However, it should be noted that the piston means 13 may be constructed of a porous material for allowing the membrane covering the oval window of the middle ear to grow thereinto thereby helping the piston means 13 to maintain its proper position relative to the oval window. Such a biocompatible porous material is manufactured under the trademark "Plasti-Pore" and is porous, high density polyethylene.

The anchor means 15 is securely attached to the first end 17 of the piston means 13 and includes a clamp member 33 for extending substantially around the incus to fixedly attach the piston means 13 to the incus. The clamp member 33 is capable of being easily bent to securely grasp the incus and is capable of maintaining that bent shape after the force causing it to be bent is removed. Preferably, the clamp member 33 of the anchor means 15 includes a first clasp portion 35 for extending around a first section of the long process of the incus and includes a second clasp portion 37 for extending around a second section of the long process of the incus. The first and second clasp portion 35, 37 are movable by force between a first position substantially away from each other for allowing the clamp member 33 to be inserted around the long process of the incus by way of the space between the first and second clasp portion 35, 37 and a second position substantially adjacent each other (see the phantom line showing of FIG. 1) for causing the clamp member 33 to securely grasp the long process of the incus. The first and second clasp portions 35, 37 are preferably substantially flat and wide (as compared to the wire loop of the Robinson patent) to prevent the possibility of pressure necrosis when the clamp member 33 securely grasps the long process of the incus. The anchor means 15 preferably includes a ring member 39 for securely attaching the anchor means 15 to the head portion 21 of the piston means 13. The ring member 39 is adapted to be received in the groove 27 of the head portion 21 of the piston means 13. The ring member 39 is preferably provided with a slot 41 extending through one side thereof and with inturned portions 43 adjacent either side of the slot 41 for extending into the aperture 29 in the head portion 21 of the piston means 13 to help secure the anchor means 15 to the piston means 13. The anchor means 15 is constructed of any material that can be easily bent into a desired shape and is able to hold that bent shape after the force causing it to be bent is removed. More specifically, the anchor means 15 is preferably constructed of a relatively rigid, non-resilient platinum metal which has sufficient malleability so that it can be easily bent by the application of slight pressure.

Referring to FIG. 5 of the drawings, the use of the stapedial prosthesis 11 of the present invention will now be explained. To replace a defective stapes with the stapedial prosthesis 11 of the present invention, the defective stapes is first removed from the middle ear using methods well known to those skilled in the art. A vein graft or like membrane 45 is then typically placed over the oval window. Next, with the first and second clasp portions 35, 37 of the clamp member 33 in said first position, the stapedial prosthesis 11 of the present invention is inserted into the middle ear and the clamp member 33 of the anchor means 15 is inserted around the long process 47 of the incus 49 by way of the space between the first and second clasp portions 35, 37. The socket 23 of the head portion 21 of the piston means 13 is then aligned with a portion of the lenticular process 51 of the incus 49 and the indent 31 in the second end 19 of the piston means 13 is positioned on the membrane 45 over the oval window. The first and second clasp portions 35, 37 are then moved with aid of forceps or the like from the first position substantially away from each other to the second position substantially adjacent each other for causing the clamp member 33 to securely grasp the long process 47 of the incus 49. The first and second clasp portions 35, 37 are preferably twisted somewhat so that they lie flat against the long process 47 of the incus 49 thereby reducing the possibility of pressure necrosis.

As thus constructed and used, the present invention provides a stapedial prosthesis 11 that can be easily, securely and safely anchored to the incus without danger of being anchored too tightly thereby creating a possibility of pressure necrosis of the incus or being anchored too loosely thereby creating a possibility of dislocation of the prosthesis. In addition, the present invention provides a stapedial prosthesis 11 that will maintain its proper position relative to the oval window under adverse conditions.

Although the invention has been described and illustrated with respect to a preferred embodiment thereof, it is not to be so limited since changes and modifications may be made therein which are within the full intended scope of the invention.

I claim:

1. A prosthesis for replacing the stapes of the middle ear, said prosthesis comprising:
    a. piston means for transmitting sound vibrations from the incus to the oval window of the middle ear, said piston means including a first end for engagement with the incus and including a second end for association with the oval window, said first end of said piston means including a socket for receiving a portion of the incus;
    b. anchor means securely attached to said first end of said piston means for anchoring said piston means to the incus, said anchor means including a clamp member for extending substantially around the incus to fixedly attach said piston means to the incus, said clamp member being capable of being easily bent to securely grasp the incus and being capable of maintaining that bent shape after the force causing it to be bent is removed, said clamp member including a first clasp portion for extending around a first section of the long process of the incus and a second clasp portion for extending around a second section of the long process of the incus, said first and second clasp portions being movable by force between a first position substantially away from each other for allowing said clamp member to be inserted around the long process of the incus by way of the space between said first and second clasp portions and a second position substantially adjacent each other for causing said clamp member to securely grasp the long process of the incus.

2. A prosthesis for replacing the stapes of the middle ear, said prosthesis comprising:
    a. piston means for transmitting sound vibrations from the incus to the oval window of the middle ear, said piston means including a first end for engagement with the incus and including a second end for association with the oval window, said first end of said piston means including a head portion, said second end of said piston means including a rod portion, said head portion having a socket for receiving a portion of the lenticular process of the incus, said socket having its longitudinal axis aligned with the longitudinal axis of said rod portion and opening opposite said second end of said piston means;
    b. anchor means securely attached to said first end of said piston means for anchoring said piston means to the incus, said anchor means including a clamp member for extending substantially around the incus to fixedly attach said piston means to the incus, said clamp member being capable of being easily bent to securely grasp the incus and being capable of maintaining that bent shape after the force causing it to be bent is removed, said clamp member including a first clasp portion for extending around a first section of the long process of the incus and a second clasp portion for extending around a second section of the long process of the incus, said first and second clasp portions being movable by force between a first position substantially away from each other for allowing said clamp member to be inserted around the long process of the incus by way of the space between said first and second clasp portions and a second position substantially adjacent each other for causing said clamp member to securely grasp the long process of the incus.

3. The prosthesis of claim 2 in which said anchor means includes a ring member for securely attaching said anchor means to said head portion of said piston means, and in which said head portion of said piston means includes a groove in its outer wall lying transverse to the longitudinal axis of said socket for receiving said ring member of said anchor means.

4. The prosthesis of claim 3 in which said second end of said piston means includes an indent on the end of said rod portion opening opposite said socket of said head portion of said piston means for allowing the membrane covering the oval window of the middle ear to grow thereinto thereby helping said piston means to maintain its proper position relative to the oval window.

5. The prosthesis of claim 4 in which said head portion of said piston means includes an aperture extending lateral from said socket through one wall of said head portion adjacent said groove for allowing access into said socket when a portion of the lenticular process of the incus is received in said socket, and in which said ring member of said anchor means is provided with a slot extending through one side thereof and includes inturned portions adjacent either side of said slot for extending into said aperture in said head portion to help secure said anchor means to said piston means.

6. The prosthesis of claim 5 in which said anchor means is composed of a platinum metal and in which said piston means is composed of a stainless steel metal.

7. The prosthesis of claim 5 in which said piston means is composed of a biocompatible porous material for allowing the membrane covering the oval window of the middle ear to grow thereto thereby helping said piston means to maintain its proper position relative to the oval window.

8. A prosthesis for replacing the stapes of the middle ear, said prosthesis comprising:

a. piston means for transmitting sound vibrations from the incus to the oval window of the middle ear, said piston means including a first end for engagement with the incus and including a second end for association with the oval window, said first end including a head portion having a socket for receiving a portion of the lenticular process of the incus, said second end including a rod portion, said socket having its longitudinal axis aligned with the longitudinal axis of said rod portion and opening opposite said second end of said piston means, said head portion having a groove in its outer wall lying transverse to the longitudinal axis of said socket and having an aperture extending lateral from said socket through one wall of said head portion adjacent said groove for allowing access into said socket when a portion of the lenticular process of the incus is received in said socket, said second end of said piston means including an indent on the end of said rod portion opening opposite from said socket of said head portion for allowing the membrane covering the oval window of the middle ear to grow thereinto thereby helping said piston means to maintain its proper position relative to the oval window; and b. anchor means securely attached to said first end of said piston means for anchoring said piston means to the incus, said anchor means including a clamp member for extending around the incus to fixedly attach said piston means to the incus, said clamp member of said anchor means including a first clasp portion for extending around a first section of the long process of the incus and a second clasp portion for extending around a second section of the long process of the incus, said first and second clasp portions being movable by force between a first position substantially away from each other for allowing said clamp member to be inserted around the long process of the incus by way of the space between said first and second clasp portions and a second position substantially adjacent each other for causing said clamp member to securely grasp the long process of the incus, said anchor means including a ring member for coacting with said groove of said head portion of said piston means for securely attaching said anchor means to said head portion of said piston means, said ring member being provided with a slot extending through one side thereof and including inturned portions adjacent either side of said slot for extending into said aperture in said head portion of said piston means to help secure said anchor means to said piston means.

9. The prosthesis of claim 8 in which said anchor means is composed of a platinum metal.

* * * * *